United States Patent [19]

Kaul et al.

[11] Patent Number: 5,493,022
[45] Date of Patent: Feb. 20, 1996

[54] BRIGHTENER AND LIGHT STABILIZER SALTS

[75] Inventors: Bansi L. Kaul, Biel-Benken, Switzerland; Angelos-Elie Vougioukas, St. Louis, France

[73] Assignee: Sandoz Ltd., Basel, Switzerland

[21] Appl. No.: 303,057

[22] Filed: Sep. 8, 1994

Related U.S. Application Data

[63] Continuation of Ser. No. 59,521, May 10, 1993, abandoned, which is a continuation of Ser. No. 687,860, May 31, 1991, abandoned.

[30] Foreign Application Priority Data

Oct. 10, 1990 [DE] Germany .......................... 39 32 914.2

[51] Int. Cl.$^6$ ................................................ C07D 251/48
[52] U.S. Cl. .................. 544/193.2; 544/196; 544/197; 544/204; 544/208; 544/209; 544/219
[58] Field of Search ................................ 544/193.2, 196, 544/197, 204, 208, 219, 209

[56] References Cited

U.S. PATENT DOCUMENTS

| | | | |
|---|---|---|---|
| 4,025,507 | 5/1977 | Fleck et al. | 544/193.2 |
| 4,115,379 | 9/1978 | Perrey et al. | 260/163 |
| 4,576,649 | 3/1986 | Oliver et al. | 106/308 |
| 4,587,195 | 5/1986 | Ishikawa et al. | 544/193.2 |
| 5,037,448 | 8/1991 | Kaul | 8/539 |
| 5,316,553 | 5/1994 | Kaul et al. | 8/639 |

FOREIGN PATENT DOCUMENTS

| | | |
|---|---|---|
| 0180116 | 5/1986 | European Pat. Off. . |
| 210172 | 5/1984 | German Dem. Rep. . |
| 2534830 | 2/1977 | Germany . |
| 3434920 | 5/1986 | Germany . |

OTHER PUBLICATIONS

Derwent Abstract of: DE343920, 1986.
Derwent Abstract of DE2534830, 1977.
Derwent Abstract of EP-180116, 1986.
Derwent Abstract of DD-210172, 1984.

*Primary Examiner*—Yogendra N. Gupta
*Attorney, Agent, or Firm*—Robert S. Honor; Carl W. Battle; Michael P. Morris

[57] ABSTRACT

Salts of organic optical brighteners or light stabilizers with compounds which contain at least one ammonium, cycloammonium or immonium group and at least one aliphatic group, cycloaliphatic group, or aromatic group bonded to at least one (up to four) carbonyl group, or heteroaromatic group. resp. basic brighteners or light stabilizers with compounds which contain a radical containing at least one carboxylic acid or sulphonic acid radical and one aliphatic, cycloaliphatic, monomeric aromatic or heteroaromatic group, or contain a $C_{2-14}$-dicarboxylic acid or amino-$C_{2-1}$-alkylcarboxylic acid radical, are eminently suitable for the brightening and light stabilizing of synthetic plastic compositions.

3 Claims, No Drawings

BRIGHTENER AND LIGHT STABILIZER SALTS

This is a continuation of application Ser. No. 08/059,521, filed May 10, 1993, now abandoned, which in turn is a continuation of application Ser. No. 07/687,860, filed May 31, 1991, now abandoned.

It has been shown that fibre material consisting of synthetic polyamides and containing brighteners resp. light stabilizers in the stock has poor wet fastness, especially poor washing fastness, the brighteners and light stabilizers diffuse disproportionately and strongly into the washing liquor, which has led to protests from the consumers.

In the course of work to eliminate this defect, it was found that the brighteners and light stabilizers of the general formula I, $$A_n \cdot (B)_n \quad (I)$$

wherein
  A is the radical of a) an anionic or b) a cationic brightener or light stabilizer,
  B in the case of a) is a radical containing at least one ammonium, cycloammonium or immonium group and at least one aliphatic group, cycloaliphatic group, or aromatic group bonded to at least one (up to four) carbonyl group, or heteroaromatic group from the series of triazine, pyrimidine, quinazoline, quinoxaline, piperazine, phthalimide or phthalazine compounds, whereby the radicals containing an aliphatic or cycloaliphatic group also contain at least one cyclically bonded ammonium group, and in the case of b) is a radical having at least one carboxylic acid or sulphonic acid radical and one aliphatic, cycloaliphatic, aromatic or heteroaromatic group, or is a $C_{2-14}$-dicarboxylic acid or amino-$C_{2-12}$-alkylcarboxylic acid radical, and the two n independently of one another, are 1, 2, 3 or 4, whereby A and B are bonded together like a salt, are eminently suitable for the brightening resp. stabilizing of synthetic materials, in particular synthetic polyamides, especially synthetic polyamides which are to be manufactured into fibre material. The invention thus relates to these compounds, their production and the said use.

The brightening resp. stabilizing effects with these compounds are very remarkable, they have quite considerably more wet fastness, especially washing fastness, than with the corresponding compounds which are not bonded as a salt to radicals B.

The compounds according to the invention are also eminently suitable for the brightening or light stabilizing of soluble synthetics, e.g. nitrocellulose lacquers.

The brightener and light stabilizer radicals A may have anionic or also cationic character. Radicals A of anionic brighteners are generally preferred. Similarly, preference is also given to the radicals B, which contain up to four, preferably one or two ammonium or immonium groups, (these are understood to include cyclically bonded ammonium, especially ammonium-nitrogen which is bonded in 2,2,6,6-tetramethylpiperidine or in piperazine radicals) and one $C_{1-12}$-alkyl, cyclohexane, piperazine, triazine, pyrimidine, quinazoline, quinoxaline, phthalazine, phthalimide or benzene bridging member, preferably a bridging member from the benzene or triazine series. Preference is thus also given to the compounds of formula I, wherein one n is 1 and the other n is 1 or 2, especially 1.

Of the radicals given for brighteners A, preference is given in particular to those of formula

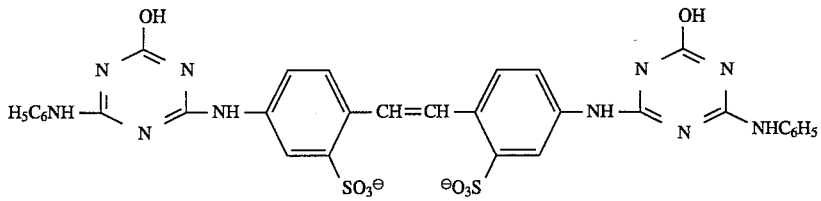

as well as the compounds described in the book by K. Venkataraman "The Chemistry of Synthetic Dyes" Vol.V, 1971 on pages 550–674, which contain acidic groups (—$SO_3H$-groups) or basic groups (e.g. ammonium, oxazolium, thiazolium, pyridinium or piperidinium groups).

The light stabilizers, in particular UV stabilizers, are understood to be especially the compounds which are known from Kirk-Othmer "Encyclopedia of Ehcmical Technology", 3rd edition, Vol. 23, pp 615–625, resp. the compounds which are known from "Ullmanns Encyklopädie der technischen Chemie", 4th edition, Vol. 15, pages 253–267, in particular 257–260, especially when the compounds are in sulphonated form.

The preferred compounds B (free amines, resp. imines, not yet bonded as salts) are those which contain one or several radicals with a sterically hindered amino-nitrogen, which are simultaneously effective as light stabilizers, especially those containing groups of formulae a to e

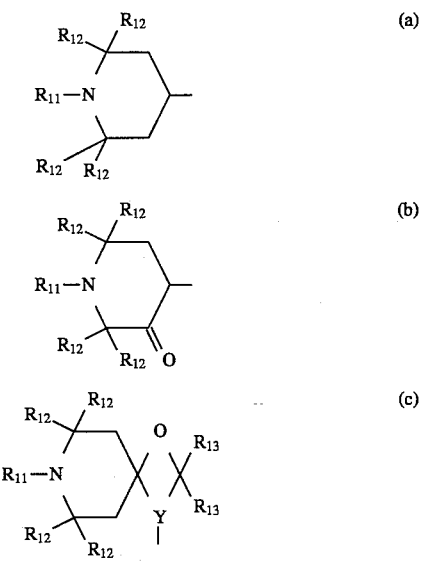

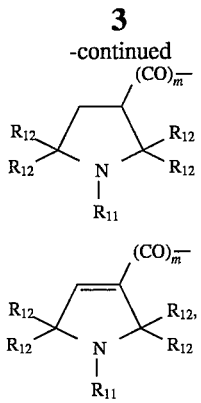

wherein
- $R_{11}$ signifies hydrogen or $C_{1-4}$-alkyl, preferably hydrogen or $C_{1-2}$-alkyl,
- all $R_{12}$ independently of one another, signify $C_{1-5}$-alkyl, preferably methyl,
- Y— signifies a group of formula —CO—N< or >N—CO— the two $R_{13}$ independently of one another, signify hydrogen, $C_{1-2}$-alkyl or one $R_{13}$ signifies phenyl and the other is hydrogen or $C_{1-2}$-alkyl or both $R_{13}$ together signify a group of formula —(CH$_2$))$_{11}$— and m signifies 0 or 1,
whereby the compounds with a group of formula a are preferred.

Preference is thus given to the compounds of formula I, wherein A is the radical of an anionic brightener and B is a radical which bears one or two 2,2,6,6-tetramethylpiperidinium or 1,2,2,6,6-pentamethylpiperidinium groups and optionally one, two or three 2,2,6,6-tetramethylpiperidyl groups or 1,2,2,6,6-pentamethylpiperidyl groups, both bonded in 4-position.

Particular preference is also given to the compounds of formula I, wherein B is benzene which is substituted by one, two or three groups of formula f and by a group, bonded by a —CO— bridge, of formula g

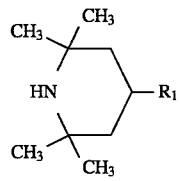

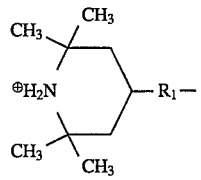

($R_1$=—O— or —NR$_2$— and $R_2$=H or $C_{1-2}$-alkyl)
or it is triazine which bears as substituents in 2-position a group of formula g, in 4-position a group of formula f and in 6-position a chlorine or similarly a group of formula f, or it is a compound of formula

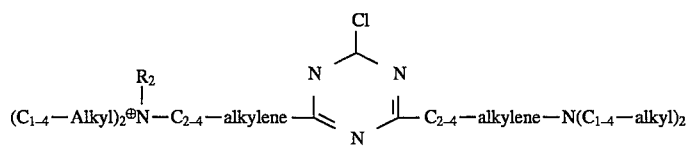

wherein $R_2$ signifies hydrogen or $C_{1-3}$-alkyl, preferably hydrogen and n is 1.

Further examples of components B (as free amino resp. cyclic amino compounds) are:

1. 1,3,5-tri-(2',2',6',6'-tetramethylpiperidyl-4')-trimesic acid triamide,
2. 2,4-bis-(2',2',6',6'-tetramethylpiperidyl-4'-amino)-6-chlorotriazine,
3. 2,4,6-tri-(2',2',6',6'-tetramethylpiperidyl-4'-amino)-triazine,
4. bis-(2,2,6,6-tetramethylpiperidyl-4'-aminocarbonyl-paraphenylene)-terephthalic acid diamide,
5. bis-(2,2,6,6-tetramethylpiperidyl-4')-terephthalic acid diamide,
6. 2,4-bis-(2',2',6',6'-tetramethylpiperidyl-4'-amino)-quinazoline,
7. 2,3-bis-(2',2',6',6'-tetramethylpiperidyl-4'-amino)-quinoxaline,
8. 1,4-bis-(2',2',6',6'-tetramethylpiperidyl-4'-amino)-phthalazine,
9. 2-chloro-4,6-bis-(2',2',6',6'-tetramethylpiperidyl-4'-amino)-pyrimidine,
10. 2,5-dichloro-4,6-bis-(2',2',6',6'-tetramethylpiperidyl-4'-amino)-pyrimidine,
11. 2-fluoro-5-chloro-4,6-bis-(2',2',6',6'-tetramethylpiperidyl- 4'-amino)-pyrimidine
12. 2,4,6-tri-(2',2',6',6'-tetramethylpiperidyl-4'-amino)-pyrimidine
13. 2,4,6-tri-(2',2',6',6'-tetramethylpiperidyl-4'-amino)-5-chloropyrimidine as well as the compounds of formulae 14.
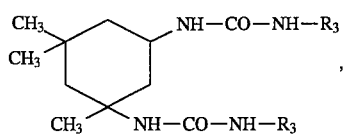
15.
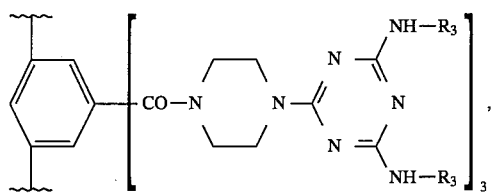
16.
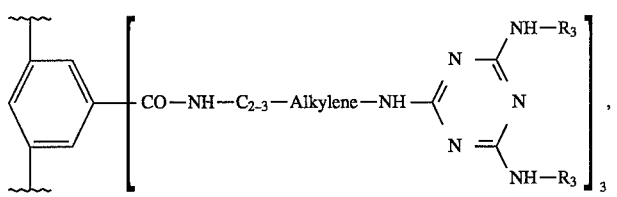
17.
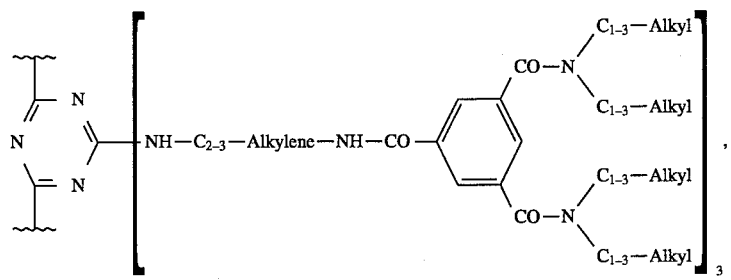
18.
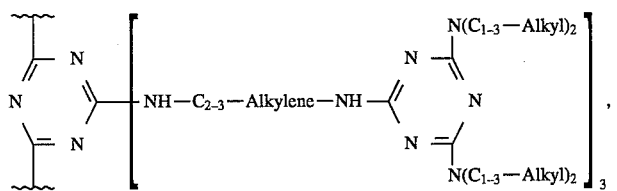
19.
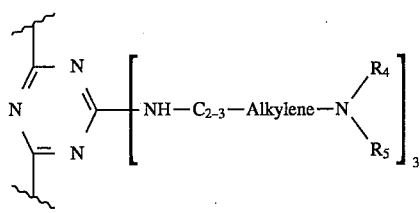
20.

-continued

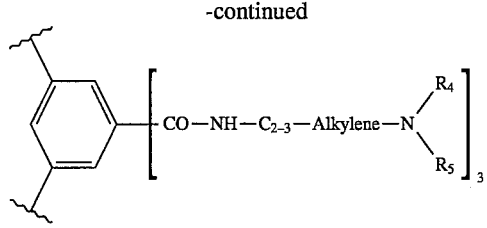

in formulae 19 and 20, $R_4$ and $R_5$, independently of one another, signify hydrogen or $C_{1-3}$-alkyl,

21.

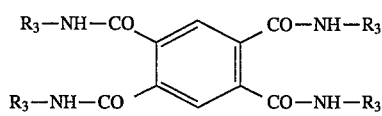

22.

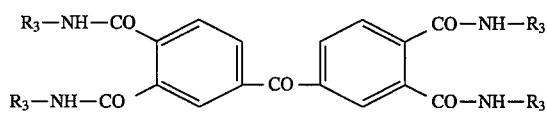

23.

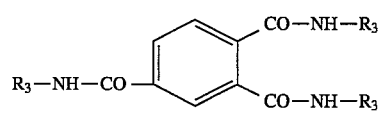

24.

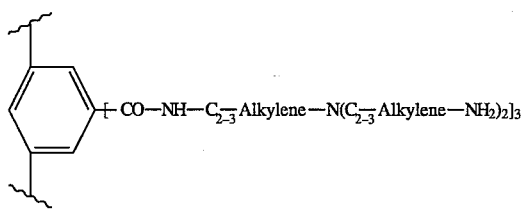

25.

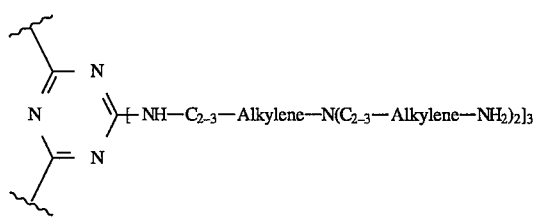

26.

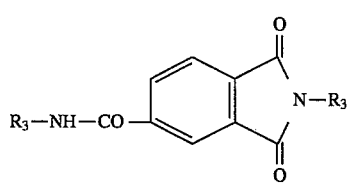

27.

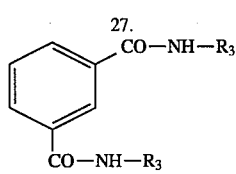

28.

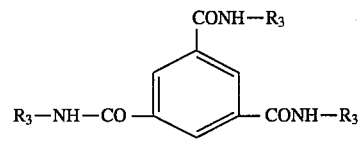

29.

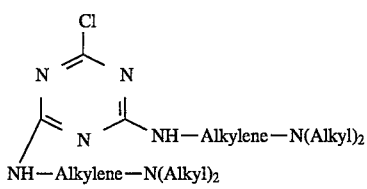

30.

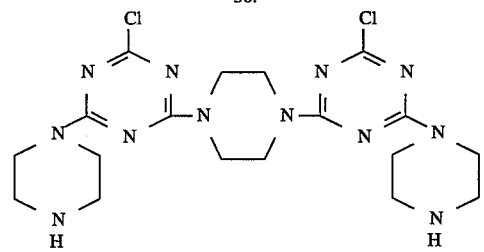

31.

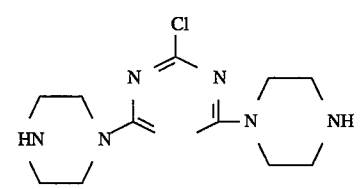

32.

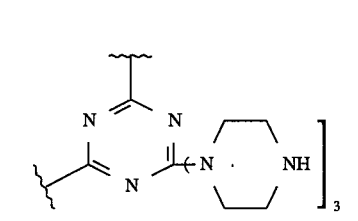

33.

$R_6(-CONH-R_3)_p$

34.

$H_2N-C_{2-12}$-alkylene $CONH-R_3$ wherein p is 1, 2, 3 or 4, preferably 1 or 2, $R_3$ is 2,2,6,6-tetramethylpiperidyl-4- and $R_6$ is a p-valent aliphatic radical with up to 12, preferably an alkyl radical with up to 6, especially 1, 2, 3 or 4 carbon atoms, whereby $R_3$ in the above formulae is always a 2,2,6,6,-tetramethylpiperidyl-4- group and in place of the —NH— bridge bonded thereto, an oxygen bridge or a bridging member of formula —N(C$_{1-2}$-alkyl)- may be located.
Preferred components B, free acids for salt formation with basic brighteners are e.g.
35.
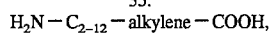
H$_2$N—C$_{2-12}$—alkylene—COOH,
36.
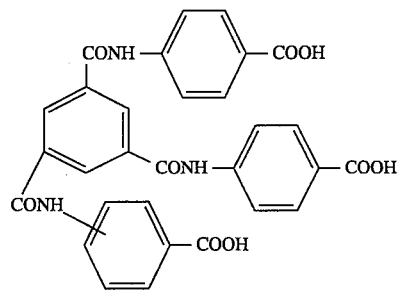
37.
4-benzoylamino-benzoic acid
38.
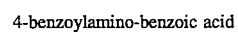
HOOC—alkylene NHCO—⟨ ⟩—CONH—alkylene—COOH
39.
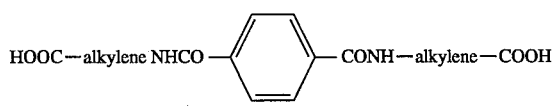
40.
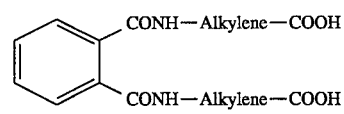
41.
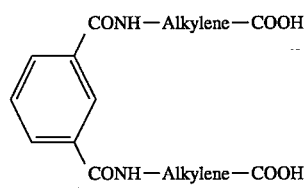
42.
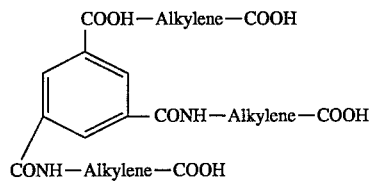
43.
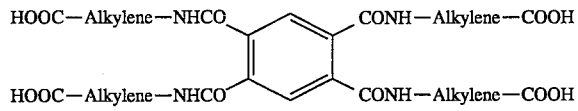
44.
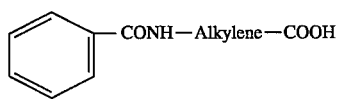

45.
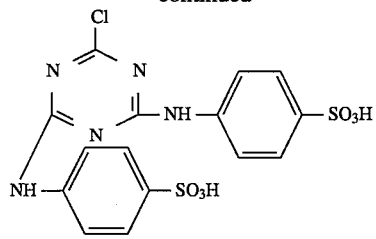

46.
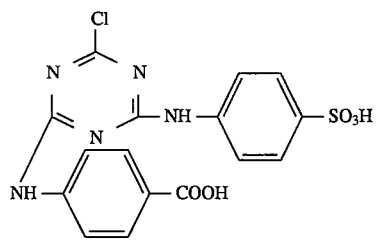

47.
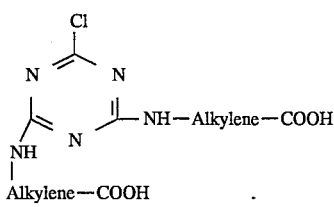

48. 2,4,-bis-(4'-carboxyphenylamino)-6-chlorotriazine,

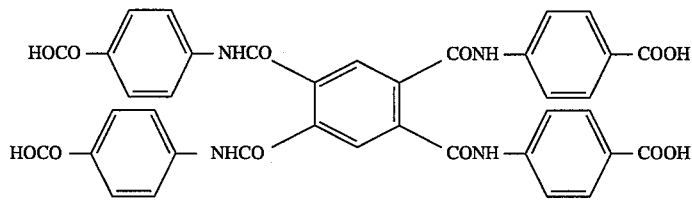

49. 1,4-bis-(4'-carboxyphenylaminocarbonyl)-benzene,
50. 1,3-bis-(4'-carboxyphenylaminocarbonyl)-benzene,
51. 1,2-bis-(4'-carboxyphenylaminocarbonyl)-benzene,
52. carboxy-$C_{1-3}$-alkylene-phenyl and
53. HOCO—$R_7$—COOH, wherein $R_7$ is the direct bond or a $C_{1-12}$-alkylene radical, whereby the said alkyl and alkylene radicals may be straight-chain or branched, and preferably (if not otherwise stated) contain 1, 2, 3 or 4, especially 1 or 2 carbon atoms.

The compounds of formulae $a_1$ to $a_{23}$ (containing acidic groups) and $b_1$ to $b_5$ may be considered e.g. as brighteners, which produce the brighteners according to the invention whilst forming a salt, together with the above-mentioned compounds, resp. those defined in patent claim 1, which exist as free bases or acids:

a1)
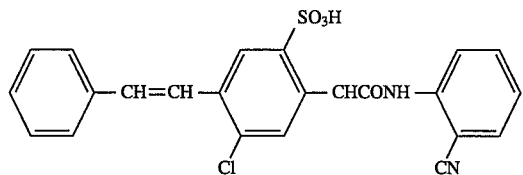

-continued
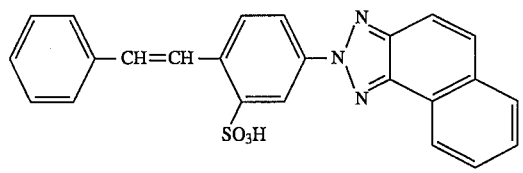
a2)
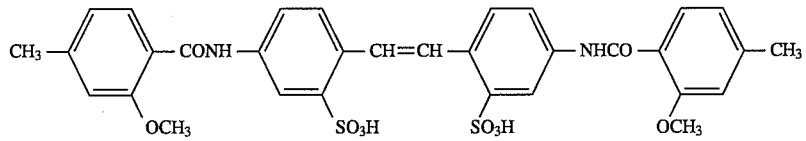
a3)
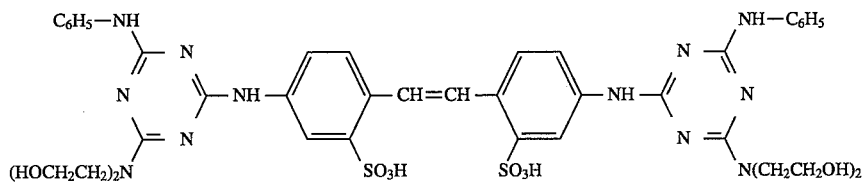
a4)
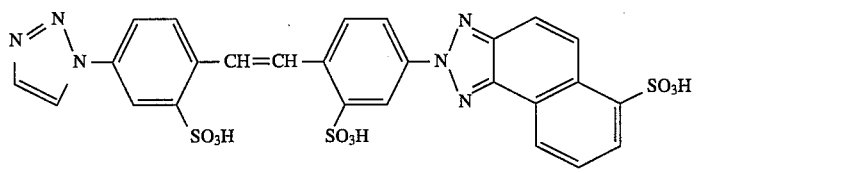
a5)
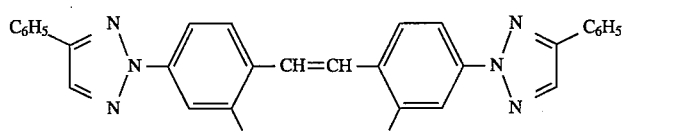
a6)
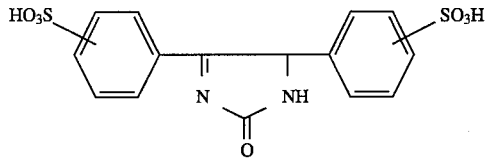
a7)
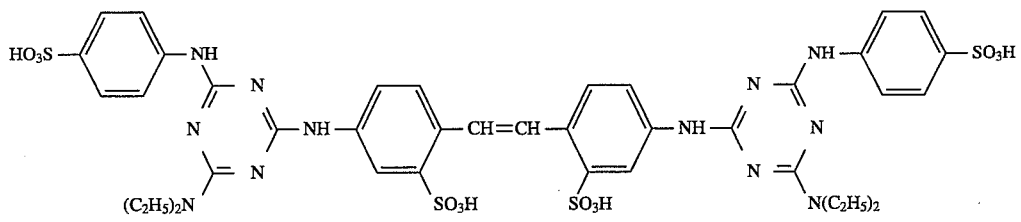
a8)
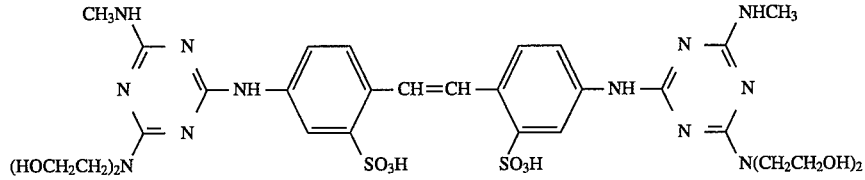
a9)
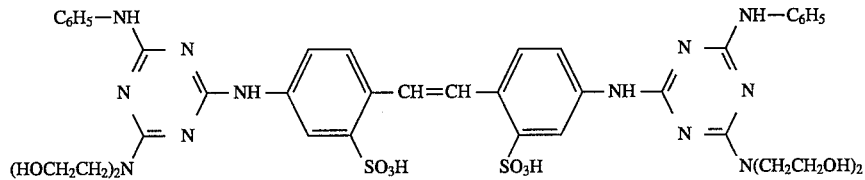
a10)

-continued
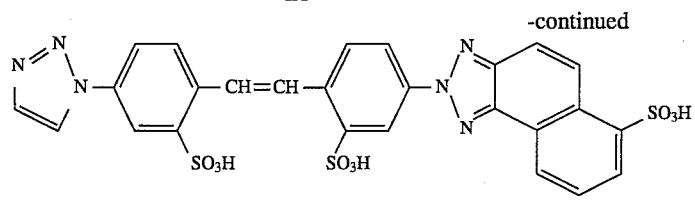 a11)
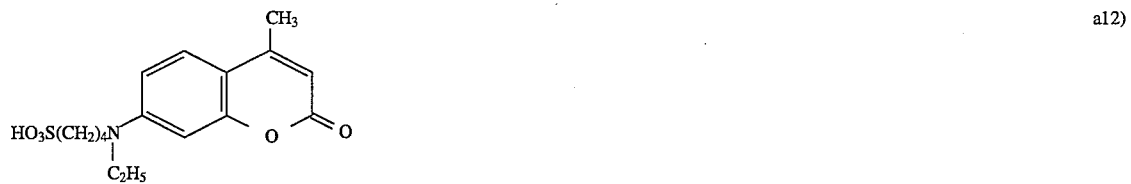 a12)
 a13)
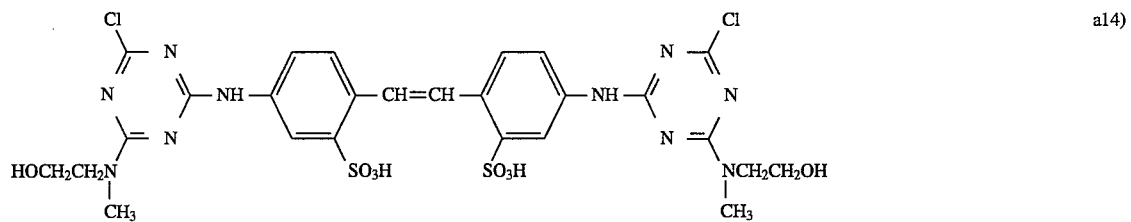 a14)
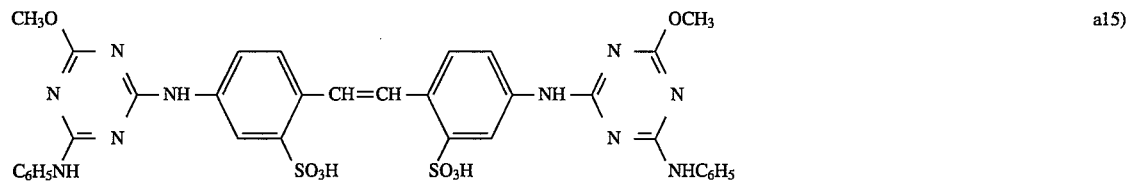 a15)
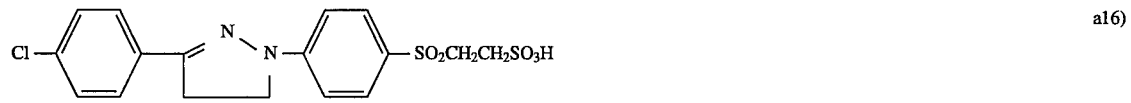 a16)
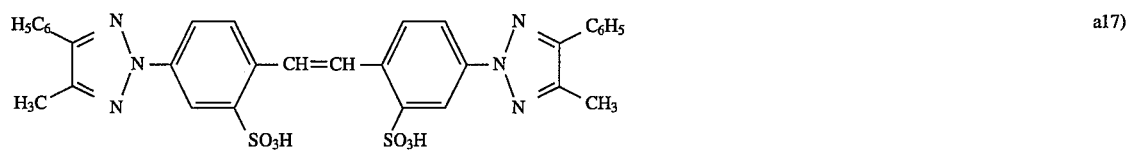 a17)
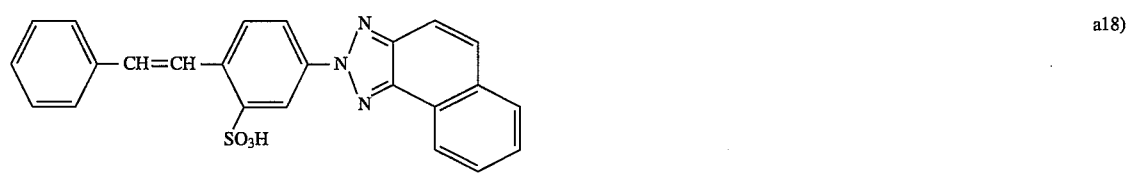 a18)
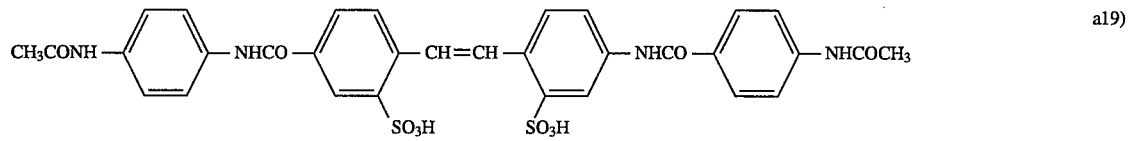 a19)
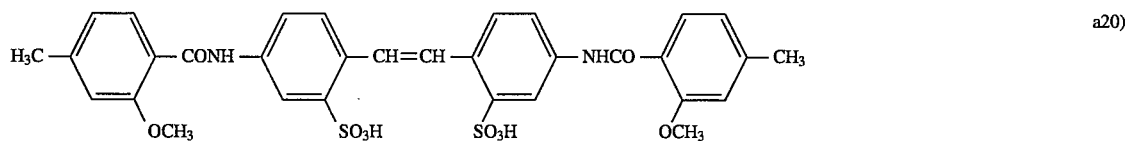 a20)

-continued
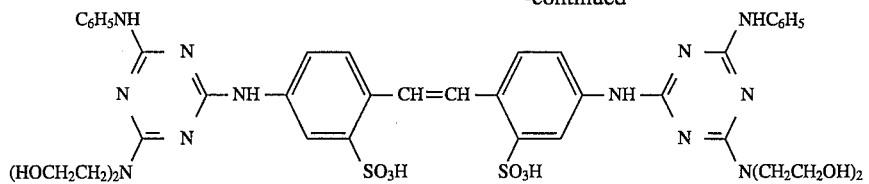
a21)
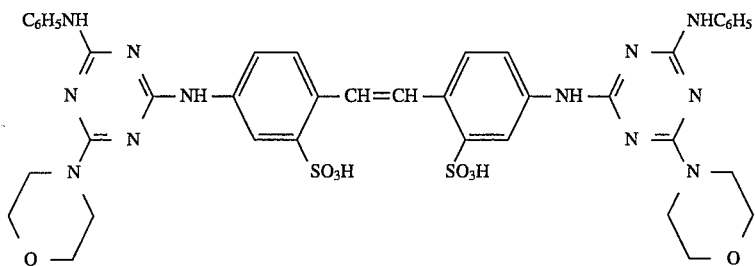
a22)
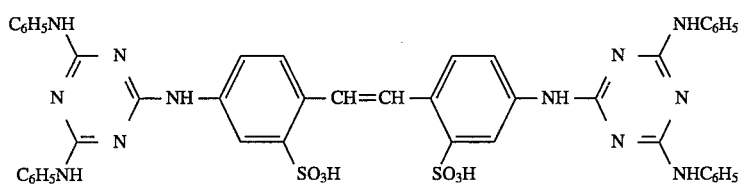
a23)
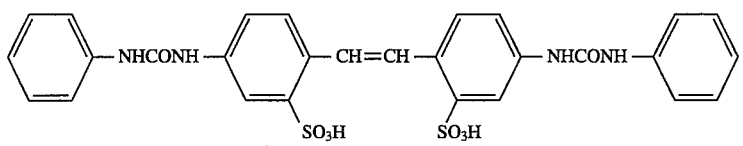
a24)
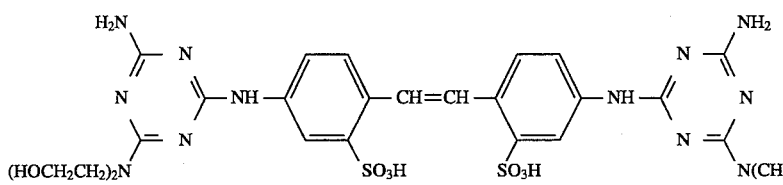
a25)
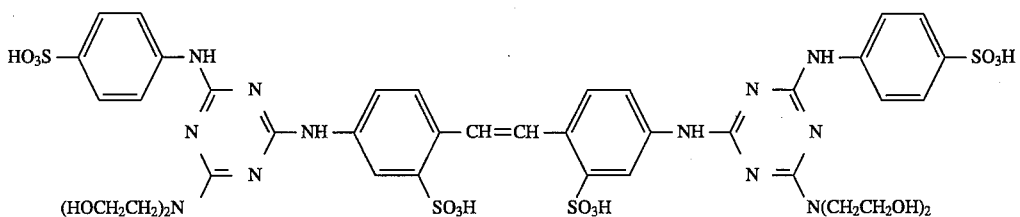
a26)
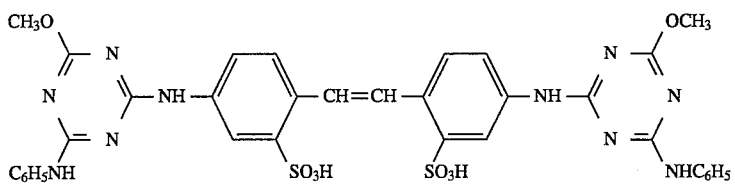
a27)
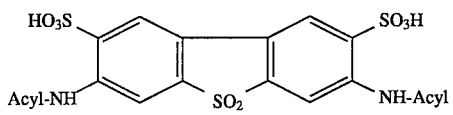
a28)
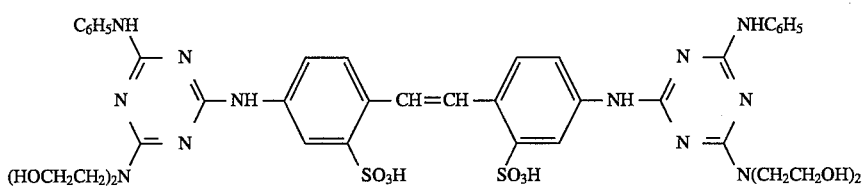
a29)

-continued
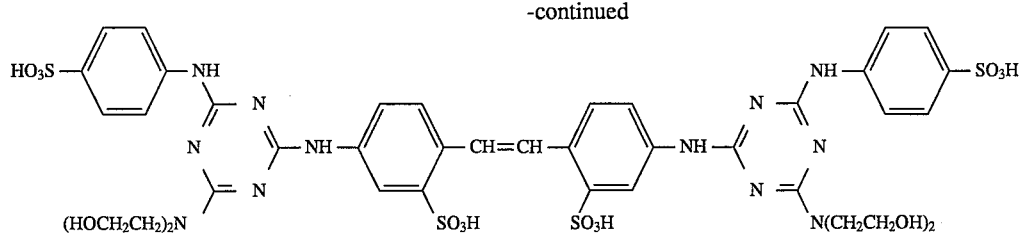 a30)
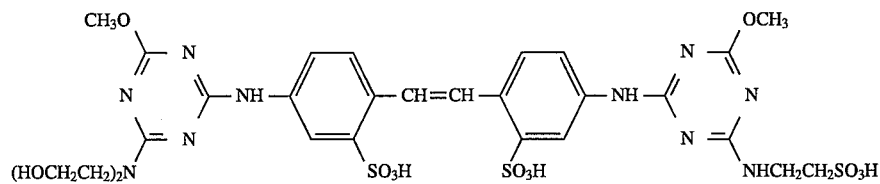 a31)
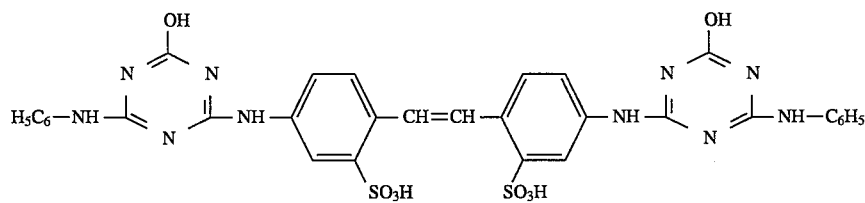 a32)
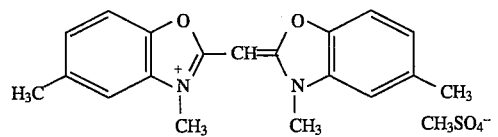 b1)
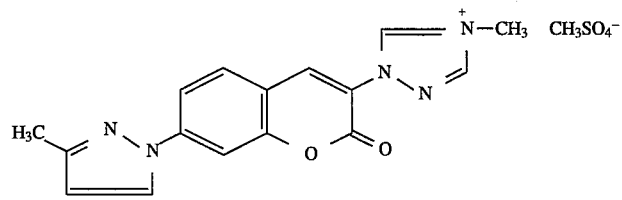 b2)
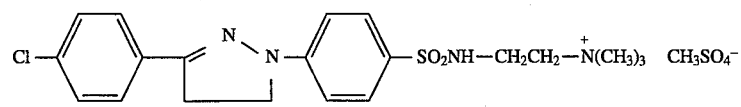 b3)
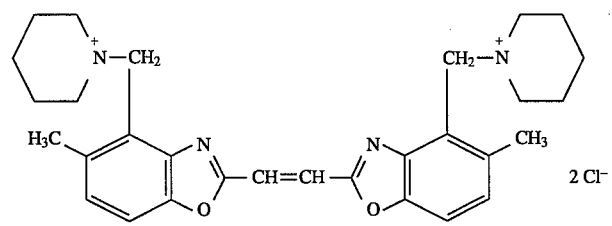 b4)
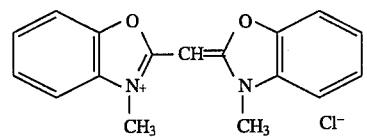 b5)
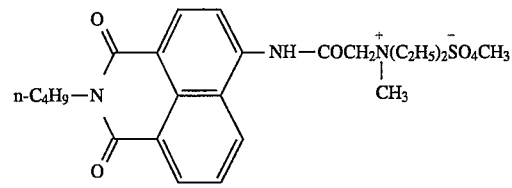 b6)

Production of components B, the amino resp. imino compounds, is effected according to processes which are familiar throughout to the specialist [amide formation from the acid chloride (e.g. trimesic acid trichloride, ex. 1) and an amine (e.g. 2,2,6,6-tetramethyl- 4-aminopiperidine), condensation of amines with triazinyl halide, etc.].

Production of the compounds (salts) of formula I similarly takes place in any manner which is familiar to the specialist. The anionic compounds can in general be reacted, just as they occur upon production (e.g. as sodium salts), in the presence of adequate amounts of a mineral acid (e.g. HCl), with the basic components B, whilst forming a salt. If the free acids are used, it is not necessary to add acid. The cationic compounds are preferably reacted in a slightly alkaline medium with the components B containing acidic groups. Mixing in the stock and usage in dissolved synthetics are effected analogously to known methods in the field of stock dyeing, resp. the field of solvent dyes.

By synthetic polyamides are understood all known synthetics of this kind, especially the polycondensates or polymerisates of dicarboxylic acids and diamines, e.g. of adipic acid and hexamethylenediamine, of lactams, e.g. ε-caprolactam, or of aminocarboxylic acids, e.g. ω-aminoundecanoic acid. Even the remaining synthetic polyamides which are generally poorly dyeable, such as those described in the book "Synthesefasern", Verlag Chemie, Weinheim; Deerfield Beach Florida; Basel, 1981 (published by Béla yon Falkai), section 6 "Charakterisierung synthetischer Fasern", can be improved by the compounds of formula I. The polyamide melt which is mixed with the compounds of formula I is shaped in the usual way, e.g. in melt spinning machines, injection moulding machines, hank spraying machines or film blowing machines.

If not otherwise mentioned, in the following examples the parts and percentages are by weight. The temperatures are given in degrees celsius.

EXAMPLE 1 a) 184.5 g of 2,4,6-trichlorotriazine are condensed in known manner with 314 g of 2,2,6,6-tetramethyl-4-aminopiperidine.

b) 45.5 g of a commercial form (85% active substance) of the brightener of formula

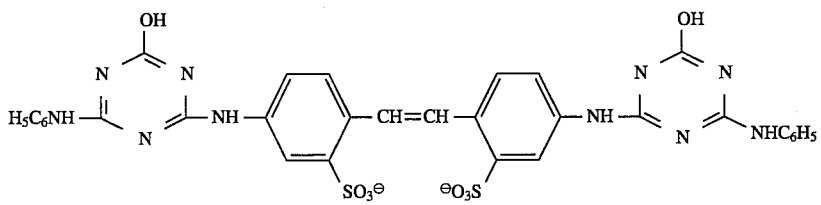

are stirred into 100 ml of water, adjusted to pH 12 with NaOH (diluted) and slowly mixed whilst stirring with a mixture of 21.2 g of the condensate obtained under a) [2,4-bis-( 2',2',6',6'-tetramethylpiperidyl-4'-amino)-6-chlorotriazine], 50 ml of water and 10 ml of HCl (30%). Stirring continues for 1 hour, the solid obtained (the piperidinium salt of the brightener) is filtered off, washed with water until free from salt, and dried.

EXAMPLE 2

Analogously to the manner described in example 1, 1 mol equivalent of the brightener of formula b 2 (above) is brought to reaction with 1 mol equivalent of the compound of formula

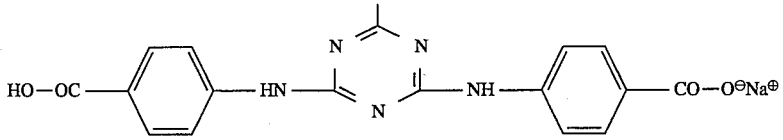

whilst forming a salt, then the insoluble salt is filtered off, washed until free from salt and dried.

EXAMPLE 3

122 parts of the light stabilizer of formula

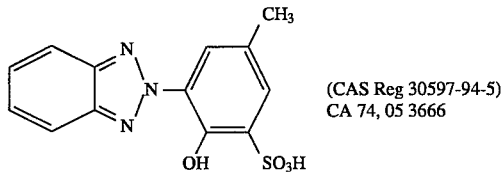

(CAS Reg 30597-94-5)
CA 74, 05 3666 are dispersed in 500 parts of water together with 88.4 parts of bis-(2,2,6,6-tetramethylpiperidyl-4)-terephthalic acid diamide (compound 5, above), and heated for 5 hours at 50° whilst stirring. The insoluble reaction product is filtered off, washed out with cold water and vacuum dried. A 2:1 salt is obtained, which has excellent stabilizing properties for synthetic compositions, especially polyamide.

EXAMPLE 4

The procedure is as given in example 3, but only 61 parts of light stabilizer (as above) are reacted with 84.7 parts of compound 2[-2,4-bis-(2',2',6',6'-tetramethylpiperidyl-4-amino)- 6-chlorotriazine] to form a 1:1 salt, and thus a compound with similar properties is obtained.

EXAMPLE 5

The procedure is as given in example 3, but instead of the 88.4 parts of terephthalic acid diamide, 161.2 parts of compound 21 (above, pyromellitic acid tetramide) are used.

The salt thus obtained has excellent light-stabilizing properties, as those of examples 3 and 4, and even under extreme conditions does not migrate from the synthetic material which has been stabilized.

EXAMPLE 6

The procedure is as given in example 5, but only 61 parts of the light stabilizer (benzotriazole compound) are used. The product obtained has very similar properties to that of examples 3 to 5.

EXAMPLE 7

Analogously to the method of example 3, 67.3 parts of the compound of formula

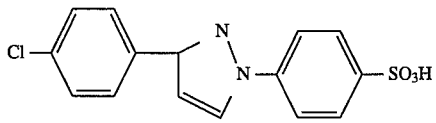

and 84.7 parts of 2,4-bis-(2',2',6',6'-tetramethylpiperidyl-4-amino)- 6-chlorotriazine (=compound 2, above) are reacted to a salt. A brightener with very good washing fastness is thus obtained. It also has a very positive influence on the light stability of the polymers treated with it.

EXAMPLE 8

The procedure is as given in example 7, but 134.6 parts of the pyrazoline compound are used. The result is a very effective brightener, which also greatly improves the light stability of the polymers treated with it.

EXAMPLE 9

The procedure is as given in example 7, but instead of the 84.7 parts of triazine compound, 88.4 parts of the compound of formula 5 (example 3) are used, and a brightener with light-fastness-improving properties is obtained.

EXAMPLE 10

According to the method of example 9, but using 134.6 parts (instead of 67.3 parts) of the pyrazoline compound, a brightener is obtained, which when incorporated into polyamide masses has very good light and washing fastness.

EXAMPLE 11

As described in example 7, but using 161.2 parts of compound 21 (pyromellitic acid tetramide), a brightener with improved light and washing fastness is similarly obtained.

EXAMPLE 12

As described in example 8, but using 161.2 parts of compound 21 (pyromellitic acid tetramide) instead of 84.7 parts of triazine compound, a brightener with very similar properties is obtained.

Analogously to the methods in the previous examples, the compounds of formulae 1 to 34 can also be reacted with brighteners containing acidic groups (formulae $a_1$ to $a_{31}$), resp. the compounds of formulae 35 to 55 with basic brighteners (of formulae $b_1$ to b), to form the brightener salts according to the invention.

APPLICATION EXAMPLE 1

100 parts of poly-ε-caprolactam in powder form are mixed in a drum mixer with 1 part of the brightener salt of example 1. After a short time, the powder disperses very evenly. After ca. 10 minutes, the mixture is dried for 16 hours at 120° C., placed in a melt spinning machine, and after a retention time of 8 minutes at 275°–280° C. in a nitrogen atmosphere is spun into fibres. The brightening effect obtained is extremely fast to light and washing. In a washing fastness test carried out for comparison, it was shown that the brightening effect of the fibres treated according to the invention, after washing (1% detergent, 1 hour at 70°), was more than 12 times greater than that of fibres which had not been mixed in the stock with the salted brightener (according to the invention).

APPLICATION EXAMPLE 2

5 parts of the dyestuff salt of example 2 with a dissolver are stirred into 95 parts of a nitrocellulose lacquer, produced from 18.8% of nitrocellulose A15 moistened with 35% isopropanol (in the form of white flocks), 6.3% of acrylic acid butyl ester polymers, softener resin (Acronal 4F, BASF), 3.3% of diphenyloctyl phosphate, softener (Santicizer 141, Monsanto), 10.0% of methoxypropanol (Dowanol PM, Dow Chemical), 41.6% of ethanol, 10.0% of ethoxypropanol and 10.0% of ethyl acetate, and dissolved over night on a rolling frame. The solubility is perfect.

Wet films with the above lacquer composition were produced with a 25 μm doctor blade on a) unlacquered aluminium foil and b) on aluminium foil lacquered with colourless nitrocellulose lacquer, these were dried for 5 hours at 130° C. The transparency was determined as a measure of the compatibility of the dyestuff salt with the solvent-free film, and the adhesive strength was determined by the Scotch tape test on the unlacquered and on the previously lacquered aluminium foil. Both properties were judged to be perfect.

I claim:

1. The brighteners and light stabilizers of formula I, $$An.Bn \quad (1)$$

wherein A is a radical of the formula

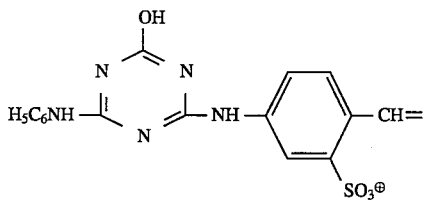

-continued

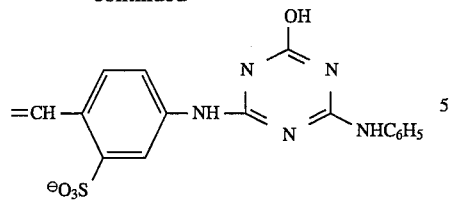

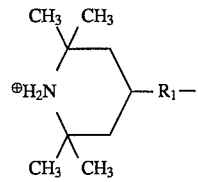

and B, is a radical containing at least one cycloammonium or immonium group and at least one aliphatic group, cycloaliphatic group, or aromatic group bonded to at least one carbonyl group, or heteroaromatic group from the series of triazine, pyrimidine, quinazoline, quinoxaline, piperazine, phthalimide, or phthalazine compounds, whereby the radicals containing an aliphatic or cycloaliphatic group also contain at least one cyclically bonded ammonium group, and both n, independently of one another, are 1, 2, 3, or 4, whereby A and B are bonded together like a salt.

2. The brighteners and light stabilizers of formula I, according to any one of the preceding claims, wherein A is the radical of an anionic brightener and B is a radical which bears one or two 2,2,6,6-tetramethylpiperidinium groups and optionally one, two or three 2,2,6,6-tetramethylpiperidyl groups, always in 4-position.

3. The brighteners and light stabilizers of formula I, according to any one of the preceding claims, wherein A is the radical of an anionic brightener or light stabilizer, and B is benzene which is substituted by one, two or three 2,2,6,6-tetramethylpiperidyl-4-oxycarbonyl or one, two or three 2,2,6,6-tetramethylpiperidyl-4-aminocarbonyl groups, and by a group, bonded by a —CO— bridge, of formula (g)

wherein $R_1$=—O— or —$NR_2$— and $R_2$=H or $C_{1-2}$-alkyl or it is triazine which bears as substituents in 2-position a group of formula (g), and in 4-position a group of formula (f)

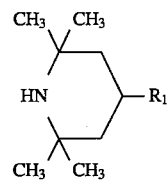

and in 6-position a chlorine or it is a compound of formula

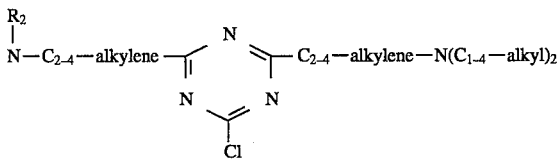

wherein $R_2$ is H or $C_{1-2}$alkyl and n is 1.

* * * * *